United States Patent
Wolfrum et al.

(10) Patent No.: US 9,638,693 B2
(45) Date of Patent: May 2, 2017

(54) METHOD FOR PRODUCING A NANOPOROUS LAYER ON A SUBSTRATE

(71) Applicant: FORSCHUNGSZENTRUM JUELICH GMBH, Fachbereich Patente (DE)

(72) Inventors: Bernhard Wolfrum, Aachen (DE); Alexey Yakushenko, Aachen (DE); Andreas Offenhaeusser, Eynatten (BE); Dirk Mayer, Frechen (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 7 days.

(21) Appl. No.: 14/436,301

(22) PCT Filed: Oct. 4, 2013

(86) PCT No.: PCT/DE2013/000567
§ 371 (c)(1),
(2) Date: Apr. 16, 2015

(87) PCT Pub. No.: WO2014/063670
PCT Pub. Date: May 1, 2014

(65) Prior Publication Data
US 2015/0241418 A1   Aug. 27, 2015

(30) Foreign Application Priority Data
Oct. 27, 2012   (DE) .......... 10 2012 021 222

(51) Int. Cl.
*G01N 33/04* (2006.01)
*B05D 3/00* (2006.01)
*C23C 4/04* (2006.01)
*G01N 33/543* (2006.01)
*B82Y 40/00* (2011.01)
(Continued)

(52) U.S. Cl.
CPC .......... *G01N 33/5436* (2013.01); *B05D 3/007* (2013.01); *B22F 7/004* (2013.01); *B82Y 40/00* (2013.01); *C23C 4/04* (2013.01); *C23C 24/08* (2013.01); *B22F 1/0018* (2013.01); *B22F 2999/00* (2013.01); *B82Y 15/00* (2013.01); *Y10T 428/249978* (2015.04)

(58) Field of Classification Search
USPC ......................................... 427/201, 186, 180
See application file for complete search history.

(56) References Cited

U.S. PATENT DOCUMENTS 6,277,448 B2 * 8/2001 Strutt .......................... 427/446
6,676,904 B1 * 1/2004 Lee ...................... G01N 33/537
                                                    422/186.1

(Continued)

FOREIGN PATENT DOCUMENTS

DE   2 484 805   8/2012

OTHER PUBLICATIONS

Nanoporous thin films with controllable nanopores processed from vertically aligned nanocomposites—Zhenxing Bi, et al., Nanotechnology 21 (2010) pp. 1-8.

(Continued)

*Primary Examiner* — Cachet Sellman
(74) *Attorney, Agent, or Firm* — Norris McLaughlin & Marcus, P.A.

(57) ABSTRACT

The invention relates to a method for producing a nanoporous layer on a substrate.

13 Claims, 2 Drawing Sheets

○ 125 nm gold nanoparticles
• 12 nm gold nanoparticles
▢ Glass substrate

(51) Int. Cl.
*C23C 24/08* (2006.01)
*B22F 7/00* (2006.01)
*B22F 1/00* (2006.01)
*B82Y 15/00* (2011.01)

(56) References Cited

U.S. PATENT DOCUMENTS

| | | | |
|---|---|---|---|
| 7,306,753 B2 | 12/2007 | Kuhstoss et al. | |
| 8,137,442 B2* | 3/2012 | Pintault | C23C 4/11 |
| | | | 210/500.21 |
| 2006/0088567 A1* | 4/2006 | Warner | A61L 27/34 |
| | | | 424/422 |
| 2009/0304996 A1* | 12/2009 | Kishikawa | B32B 5/16 |
| | | | 428/141 |

OTHER PUBLICATIONS

Sintering of Porous Materials Kathy Lu, et al., ; pp. 115-1360
Ricardo H. R. Castro—Klaus van Benthem (Sintering—Mechanisms of Convention Nanodensification and Field Assisted Processes—2 pgs)—DOI: 10.1007/978-3-642-31009-6.6—(2013).
Hong Young-Kyu et al: "Controlled two-dimensional distribution of nanoparticles by spin-coating method", Applied Physics Letters, American Institute of Physics, US, vol. 80, No. 5, Feb. 4, 2002 (Feb. 4, 2002), pp. 844-846, XP012031471 ISSN: 0003-6951, DOI: 10.1063/1.1445811—the whole document.
Mukherjee et al. (Mukherjee, B., Viswanath B., and Ravishankar, N. (2010). Functional nanoporous structures by partial sintering of nanorod assemblies Journal of Physics D: Applied Physics, vol. 43, 455301 (pp. 1-6).
Buffat, O., Borel, J.-P. (1976). Size effect on the melting temperature of gold particle. Phys. Rev. A, 13, 2287-2298.
Allen, G.L., Bayles, R.A., Gile, W.W., Jesser, WA (1986). Small Particle Melting of Pure Metals Thin Solid Films, 44, pp. 297-308.
Liang, L.H., Shen, C.N., Du, S.X., Liu, W.M., Xie, X.D., Gao, HJ. (20040 Increase in Thermal Stability Induced by Organic Coatings on Nanoparticles. Physical Review B, 70, 205419 (pp. 1-5).
Amert, A.K., Oh, D.-H., Kim, N.-S. (2010) A Simulation and Experimental Study on Packing of Nanoinks to Attain Better Conductivity. Journal of Applied Physics., 108, 102806 (pp. 1-5).

* cited by examiner

METHOD FOR PRODUCING A NANOPOROUS LAYER ON A SUBSTRATE

The invention relates to a method for producing a nanoporous layer on a substrate.

BACKGROUND OF THE INVENTION

It is known from Mukherjee at al. (Mukherjee, B. Viswanath B. and Ravishankar, N. (2010). Functional nanoporous structures by partial sintering of nanorod assemblies, Journal of Physics D: Applied Physics, Volume 43, 455301 (6pp)) that it is possible to sinter nanostructures and generate defined pores by coordinated temperature controls. The pores were generated by partial melting and rounding by subsequent sintering of nanorod edges, which as a result of anisotropic heat distribution were hotter than the remaining nanorod structures. This approach theoretically allows functional surfaces to be preserved on portions of nanorods that were not melted and sintered, The melting point of a nanoparticle differs from the melting point of the native material in bulk. As a result of the higher surface-to-volume ratio, the melting temperature is lowered drastically as a function of the particle size. This connection was shown by Buffat and Borel for nanoparticles made of gold (Buffat, O., Borel, J.-P. (1976). Size effect on the melting temperature of gold particle. Phys. Rev, A, 13, 2287-2298). It was demonstrated that particles having a diameter smaller than 100 nm begin to melt at lower temperatures than would be expected based on the melting point of pure gold in bulk at 1337 K. The melting point of particles smaller than 5 nm is below 350 K. Similar results were also shown by Allen at all for other materials, such as indium, tin, bismuth and lead, (Allen, G. L., Bayles, R. A., Gile, W. W., Jesser, W A (1986). Small particle melting of pure metals. Thin Solid Films, 44, 297-308). The melting point is also influenced by the stabilizing shell of the nanoparticles or solvents in which the particles are dissolved (Liang, L. H., Shen, C. M., Du, S. X., Liu, W. M., Xie, X. C., Gao, H J. (2004). Increase in thermal stability induced by organic coatings on nanoparticles. Physical Review 8, 70, 205419 (5 pp)).

It is known from Amert et al. (Amert, A. K., Oh, D. -H., Kim, N. -S. (2010). A Simulation and experimental study on packing of nanoinks to attain better conductivity. Journal of Applied Physics, 108, 102806 (5pp)) to consecutively sinter two different materials so as to generate a particularly densely packed structure on a substrate.

Various methods are known for producing nanoporous thin films having different layer thicknesses in the range of several nanometers to several micrometers, and pore sizes from one nanometer to hundreds of nanometers. The special characteristic of these materials is the large surface-to-volume ratio, A multitude of pores increases the available active or functional surface per unit of volume compared to planar thin films.

This phenomenon can be an advantage in various areas. One known example is immunosensors for infectious diseases. These sensors take advantage of specific binding reactions between antibodies and antigens. Antigens bound to the surface can specifically bind antibodies present in an analyte, such as in the blood or in saliva, and vice versa. The signals generated by the binding reactions can be read out, for example optically by adsorption and the refractive index, or electrochemically, such as by way of a change in impedance, or by Faraday or capacitive effects. In this way, the concentration of antibodies is determined. Nanoporous structures serving as electrodes on immunochemical sensors can produce signal amplification, and thus render the sensors more sensitive, at the same sensor volume or lateral sensor surface. The larger the electrode surface, the more antibodies are able to react with antigens. In addition, non-specific binding signals of other molecules that cause noise in the system and worsen the detection threshold can be prevented by defining the sizes of the pores. Nanoporous materials can additionally be used in lab-on-a-chip systems. Due to the large surface of the active sensor electrodes, the size of the system can be reduced and the packing density of these sensors on the chip can be increased. This contributes to the ability to implement lab-on-a-chip systems comprising multiple sensor elements for various analytes.

Other applications of nanoporous materials can be found in energy storage, catalysis, membrane production, tissue engineering, photonics, adsorption, separation and drug delivery. In all these fields, the large active surface or certain pore sizes help achieve required functionality.

The methods for producing nanoporous thin films are carried out in multiple steps using chemical, mechanical or electrochemical method steps. The disadvantage is that a plurality of chemical reagents and clean room techniques are employed in the process. Anodization is one known method for producing nanoporous layers. A metal layer, for example made of aluminum, is electrochemically oxidized in an acid solution. Nanostructured films are formed as a result of self-organization.

Nanolithography is another method. Here, structures are implemented in four steps. First, a thin film of the desired material is applied to a substrate by way of chemical vapor deposition (CVD), physical vapor deposition (PVD), laser pulsed deposition (LPD) or an equivalent method. Thereafter, a thin layer of photoresist is applied, The photoresist is structured using various lithographic methods. Known methods are VIS lithography, UV lithography or EUV lithography, electron beam lithography and interference lithography. The non-cured portion of the photoresist, which is to say the cross-polymerized portion in the case of a positive method, or the softened portion of the photoresist, this being the portion having broken chemical bonds, in the case of a negative method, is removed by washing. Thereafter, the pores are transferred into the material using dry or wet etching processes. At the end of the process, the etching mask is removed.

The disadvantage is that the use of strong chemical reagents always necessitates thorough cleaning of the thin films that are produced so as to remove residues of toxic substances. This makes manufacturing with these methods complex. Production must always be carried out in multiple steps, and further requires clean room technologies for all lithographic processes. This drives up the cost and manufacturing time for the layers produced and the sensors. It is also disadvantageous that many of the described methods can only be applied to certain materials since they are dependent on certain chemical properties of the substrates.

SUMMARY OF THE INVENTION

It is the object of the invention to provide a simple and cost-effective method for producing nanoporous layers on a substrate, which can be used to produce evenly distributed pores on a substrate in a defined manner. It is a further object of the invention to provide a nanoporous layer that has defined pores evenly distributed on a substrate.

The object of the invention is achieved by the method according to claim 1 and by the nanoporous layer according to the additional independent claim. Advantageous embodiments will be apparent from the respective claims dependent thereon.

A method was developed based on the physical parameters of the materials used. At least two types of particles A and B and the physical parameters thereof
1. size and shape of particles A and B,
2. weight ratio A:B and
3. melting points of the materials A and B at a particular particle shape and size (see 1.)
are used so as to evenly provide pores on the substrate that are defined with respect to size and shape.

The following method steps are carried out in the production of the nanoporous layer on a substrate:
a) a selecting at least two particle types A and B;
b) suspending both types A and B together in a solvent;
c) applying the suspension to the substrate;
d) heating, in a controlled manner, the suspended particles A and B on the substrate by bringing the temperature close to the melting point $S_{mB}$ of the particles having the lower melting point, without reaching the melting point $S_{mA}$ of the particles having the higher melting point, or without melting the particles having the higher melting point; and
e) checking the porous surface.

Regarding a), the at least two particle types A and B are selected based on the difference in the melting points thereof. The melting point is dependent in each case on the shape and size of the particles A and B and on the chemical composition thereof. Small particles B having the same shape have a lower melting point than larger particles made of the same material, for example. The melting points of the particles are known to a person skilled in the art or are determined empirically. The difference between the melting points $S_A$ and $S_{mB}$ of types A and B should be large enough that, depending on step d) of the method according to the invention, controlled sintering is possible without melting the material having the higher melting point. In general, the difference in the melting points of the at least two materials can be just a few Kelvin, for example 20K, 19K, 18K, 17K, 16K, 15K, 14K, 13K, 12K, 11K, 10K, 9K, 8K, 7K, 6K, 5K, 4K, 3K, 2K or 1K, or the corresponding intermediate values. There should be a difference of at least 1K in the melting points of the two particle types, as the method is otherwise difficult to control in step d).

The method for producing nanoporous layers is based on a mixture of different particles, comprising at least two types of nanoparticles A and B having different melting points.

Particles A and B are understood to mean objects that have different shapes and/or sizes, and/or that are made of different materials.

The shape of the particles can be identical and can be, for example, round, cylindrical, rectangular, star-shaped, or filamentary. The shape of the particles A and B can also be different, which is to say round, cylindrical, rectangular, star-shaped, filamentary and the like.

This influences the melting point. It is possible, within the scope of the invention, to use particles A and B that have different shapes, but are otherwise made of the same material and have a substantially identical size.

It is likewise possible to select particles A and B in which the size is different (for example, size A: 100 nm and size B: 5 nm) but wherein the particles otherwise have the same shape (for example, round, star-shaped or the like, see above) and are made of the same material (such as gold).

The size of the particles A and B is, in particular 1 nm to 10 μm, in particular 1 nm to 100 nm, in particular 10 nm to 90 nm, in particular 20 nm to 80 nm, in particular 25 nm to 75 nm, in particular 30 nm to 70 nm, and particularly advantageously 40 nm to 50 nm. The larger particles A should, in particular, have a diameter of 10 to 150 nm, and advantageously of 30 to 130 nm. The smaller particles B should, in particular, have a value between 1 and 50 nm, and particularly advantageously a particle size of 5 to 30 nm should be produced.

Both the size and the shape of particles A and B influence the melting point of the respective particles. The chemical material itself also results in a difference in the melting point of the particles.

It is not necessary to select different chemical materials for the two particle types, as long as other causes result in a difference in the melting point of $S_{mA}$ and $S_{mB}$ and this is sufficiently large for the temperature program to be employed. It is readily conceivable to select different materials for the particle types A and B, so that a difference in the melting points of particles A and B is caused solely by the material. It is thus possible to select different materials for the particles A and B, for example different metals, semiconductors, ceramics, polymers, in each case with or without functional coating of the surface of the particles. Particles A and B can thus be made of either an identical chemical material, or of different chemical materials.

The nanoparticles A and B and the like, can be made of one or more materials and have different inner structures, which is to say pure cores, which are filled with a solid or liquid material or are empty, or made of cores having one or multiple shells as functional or protective layers, and chemical or biochemical termination and functionalization on the surface of the nanoparticles or in one of the inner shells.

Particles A and B can optionally comprise a central core and additional functional shells or protective shells made of the same material or different materials. Particles A and B can thus comprise chemical or biochemical terminations and functionalizations on the particle surface. This is particularly important for the further adaptation of the nanoporous layer and the use thereof as a biosensor or immunosensor.

The materials that are used in particular for particle types A and B and the like are materials used in semiconductor technology and have good conductivity. These include, in particular, but without limitation to, the following materials: gold, silver, platinum, aluminum, aluminum oxide, silicon, copper, chromium, carbon, silver chloride, titanium, titanium oxide, iron oxide, magnesium oxide, zinc oxide, silicon oxide, silicon nitride and polyaniline. It is important that the particle types A and B, and optionally further particle types that form the nanoporous layer, are made of material having good conductivity for conducting the measured signals.

The dependence of the melting point of particles A and B on the respective particle size and particle shape, as well as the chemical material, is used to generate the nanoporous structure on the substrate.

The weight ratio of particles A:B wt/wt is likewise important for forming the nanoporous layer and the shape thereof. This should be approximately 5:1 or greater. Weight ratios between the particles of approximately 5:1 to approximately 1000000:1 are readily conceivable. This is due to the fact that the weight of spherical particles is proportional to the 3rd power of the particle radius. This means that a weight ratio of A:B of 1000000:1 corresponds only to a ratio of the diameter of 100:1, assuming an identical number of spherical particles made of the same material. The scaling of the surface-to-volume ratio of spherical particles is 1/r, where r corresponds to the radius of the particle. If the differences in the weight ratio are large, the surface-to-volume ratio is determined almost exclusively by the larger particles. Weight ratios of approximately 10:1 to approximately 1000:1, and more particularly of 20:1 to approximately 200:1 are particularly advantageous. The electrical contact between large particles is typically achieved at this ratio. At the same time, the share of small particles is still low enough not to influence the pore size.

Starting at a weight ratio of A:B of approximately 5:1 wt/wt, the collectivity of particles A is present as a matrix, in which (see step b)) the collectivity of particles B is interspersed. At very high weight ratios of A:B (above 1000000:1), it is possible that sufficient contact will not be achieved within this matrix.

Weight ratios between the particles of between 20:1 and 200:1 are particularly suitable. The particles of type A having the higher melting point $S_{mA}$ should form the matrix, and thus be present in the higher proportion on the substrate. Otherwise the small particles B will influence the pore size. In extreme cases, the pores are closed, and a densely packed, which is to say non-porous, film is found.

Essentially, the amount and shape of the larger particles A having the higher melting point determine the pore size in the nanoporous layer. The pore size depends on the packing of the particles and, for spherical particles, is in the range of approximately 0.1*r to 0.6*r, where r corresponds to the radius of particles A.

As a result of mixing particles A and B having different sizes and/or shapes and/or materials, areas made of particles having different melting points $S_{mA}$ and $S_{mB}$ are present in the layer to be formed in step d).

Regarding b), depending on the materials A and B used, a suspending agent that is suitable for both materials is selected, and the materials A and B are jointly suspended therein at the predefined weight ratio. A homogeneous suspension is generated, which thereafter is applied to the substrate so as to ensure the homogeneous distribution of particles A and B on the substrate.

At least two or more particle types having different shapes and/or sizes and/or materials are then present in the suspension.

Various solvents or binding agents can be used as solvents or binding agents for the suspension and so as to achieve the requisite solubility and viscosity for the suspension. In particular water, ethanol, methanol, isopropanol, hexane, toluene, benzene, α-terpineol, dimethyl sulfoxide, glycerol, polyvinylpyrrolidone, as well as electrolytes and physiological buffers, such as PBS, HEPES and other suspending agents and solvents commonly used by persons skilled in the art are suitable. A person skilled in the art will appropriately select the solvent based on the materials used for particles A and B.

Regarding c), any surface that has good adhesion with the nanoparticles to be sintered is considered or is selected as a substrate. The substrate is sufficiently stable for the suspension to be applied and for the sintering to be employed thereafter. In particular metals, such as gold, silver, platinum, copper and the like are suited for this purpose. However, carbon and the variants thereof, and silicon, silicon oxide, silicon nitride and other ceramics, polymers, for example, polyethylene, polypropylene, polyvinyl chloride, polystyrene, polycarbonate, polyimide, polyester, Surlyn™ and the like are also particularly suitable substrates. Paper, which is either coated or not coated with a polymer, a textile fabric, which is either coated or not coated with a polymer, or wood, which is either coated or not coated with a polymer, is also a suitable substrate. As a function of the application, the substrate thickness is freely selectable in a range of 0.01 µm to 0.1 m, depending on whether or not adhesive bonding to other layers is to be carried out later. Various techniques can be employed to apply the suspension including the particles A and B to the substrate, which is to say spin coating methods, ink jet printing methods, gravure printing methods, offset printing methods, air jet printing methods, and microfluidic methods. By adjusting the method parameters, such as the rotational speed in the case of spin coating or the drop volume in the case of the ink jet method, and by controlling the viscosity during preparation of the suspension, the thickness of the deposited layer having the particles suspended therein on the substrate is precisely controlled. After the suspended particles A and B have been applied, this is advantageously in the range of approximately 1 nm (monolayer comprising nanoparticles A and B) to approximately 10 mm.

Optionally, the substrate having the particles suspended thereon can be preheated. This step advantageously causes the suspending agent or solvent to evaporate at a temperature that is considerably lower than the melting point $S_{mB}$ of the particles B having the lower melting point. This optional heating may be necessary for certain suspensions containing particles A and B so as to remove residues of solvents and/or binding agents from the deposited layer on the substrate.

Regarding d), after the suspension comprising the nanoparticles A and B has been applied to the substrate, it is heated or sintered in a controlled manner. The sintering can be carried out by way of various methods. Heat and temperature gradients, electromagnetic radiation (EM radiation), treating the structure with various wavelengths and in various manners, such as by way of UV light (wavelength=10 to 400 nm), visible light (wavelength=400 to 800 nm) and infrared light (wavelength=0.8 to 300 µm), and using non-coherent light sources and coherent light sources (laser radiation) in continuous or pulsed form, and microwave radiation (frequency=0.3 to 300 GHz) are particularly suitable. Controlled sintering is also possible by way of pulsed electric current or high-temperature plasma sintering. The temperature can be precisely controlled by supplying energy in a controlled manner, and as a result of the sintering time, so that only the nanoparticles having the lower melting point $S_{mB}$ are sintered and liquefy. In their place, the porous structure is formed in the matrix of non-melted particles having the higher melting point $S_{mA}$. The layer that is formed is porous in the overall since the melted particles having the low melting point $S_{mB}$ form holes in the matrix of non-melted particles having the higher melting point $S_{mA}$ which extend to the substrate. The particles of type A, which only melt at higher temperatures $S_{mA}$, thus remain substantially intact. At the contact points with particles B having the lower melting temperature $S_{mB}$, the particles having the higher melting point $S_{mA}$ are merged by the formation of bridges due to local melting of the shell of the nanoparticles and due to melting of the surface of the particles having the higher melting point $S_{mA}$.

Through the use of nanoparticles having different melting points $S_{mA}$ and $S_{mB}$, thin films made of one or more chemical materials are created in keeping with the number of different materials used. The thickness of the thin film and the pore size of the nanoporous layer that is formed are essentially established by the shape and the size of the nanoparticles A and B and the like and by the weight ratio thereof. The sintering program also influences the thickness and the pore size. Long sintering times at the temperature $S_{mA}$ result in complete melting of particles B having the lower melting point $S_{mB}$.

The properties of possible functional layers on the selected nanoparticles A and B which as a matter of course are not melted, do not change during partial sintering of the particles, and thus completely retain the function thereof. Temperature-sensitive particle cores, such as cores made of gold, which are functionalized with antibodies and use sintering methods. By way of heat input using microwave radiation, only the cores are caused to melt, In contrast to gold, organic antibodies hardly absorb energy in this wavelength range. The electrical properties of the porous material that is formed can be changed by appropriately selecting the nanoparticles.

The heat input can also take place using temperature ramps in a regular oven or convection oven, or in an induction furnace. Moreover, this can also take place by way of electromagnetic radiation (EM radiation), treatment with various wavelengths (UV light=10 to 400 nm), visible light (wavelength=400 to 800 nm) and infrared light (wavelength=0.8 to 300 µm) using non-coherent light sources or laser radiation in continuous and pulsed form, by microwave radiation (frequency=0.3 to 300 GHz), by electric current, by high-temperature plasma sintering, or by a hot, inert or active (resulting in a reaction on the nanoparticle surface) solution at the desired temperature.

The time, the power and the exact type of the sintering process is established depending on the nanoparticle type (material, nanoparticle size and shape, number of different nanoparticles in the suspension) and the properties thereof, which is to say in particular the melting points. In this way, the desired pore size and shape is established in a defined manner, and an even distribution of the pores is achieved. The functionality on the surface of the nanoparticles or in the core of non-sintered nanoparticles is preserved.

Regarding e), the nanoporous layer that is formed is checked, for example by way of scanning electron microscopy or other optical methods.

The method has advantages over the known methods:
No material is lost during the process, since no etching steps and washing steps (lift-off or the like) are employed during the process.
The size and shape of the nanopores can be controlled directly by the selection of the size and type of the nanoparticles.
Nanopores made of two or more materials (alloys) can be produced by selecting nanoparticles made of different materials.
The nanoporous layer can be applied to any substrate because the binding of the nanoparticles to the substrate can be adjusted using solvents and the shell of the nanoparticles.
The method can be integrated into "printed electronics" methods using printable inks. This means that applications can be produced very flexibly and cost-effectively based on this technique.

All steps can be carried out multiple times so as to generate thin films having different thicknesses or functionalities.

The nanoporous layers thus produced show differences compared to the nanoporous structures known from the prior art.
The structures have a distribution in terms of size and shape, which is to say there are nanopores or nanochannels having defined sizes and shapes. This distribution of the pore size is broader than that which is achieved, for example, by precise lithographic methods.
The size and shape of the nanopores are controlled directly by the selection of the size and type of the nanoparticles.
Nanopores made of two or more different materials (alloys) can be produced by selecting nanoparticles made of different materials.
The particles A are electrically connected to each other by and via the melted particles B, whereby a nanoporous electrode is formed.

The method according to the invention is not limited to this. Rather, it is a further object of the present invention to subject the method according to the invention according to steps a) to e) to further modification. So as to impart certain functionalities, the produced thin films or electrodes can be further modified by wet-chemical methods or by other methods, such as by plasma applications, by electrolysis methods and the like, so as to establish the desired chemical, biological or physical properties of the deposited and sintered porous thin film.

In particular, loading the nanoporous layer with antigens or antibodies can be carried out so as to provide immunosensors.

Exemplary Embodiment

The invention will be described in greater detail hereafter based on an exemplary embodiment, without thereby limiting the invention.

DESCRIPTION OF THE PREFERRED EMBODIMENTS

Figure 1:
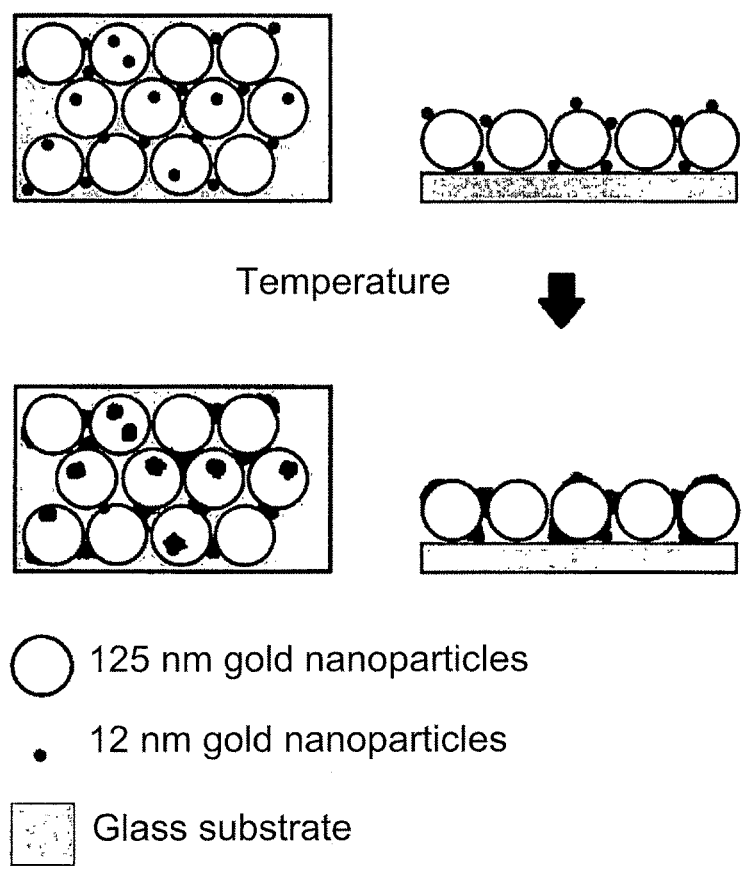
FIG. 1 shows a schematic illustration of the method according to the invention.

The top view on the left of the image in FIG. 1 shows the suspension applied to the substrate.

Two different particle types A and B are selected for the production of a nanoporous layer. The first type of nanoparticles B are round homogeneous gold nanoparticles having an average diameter of 10 nm and a protective layer made of oleylamine. The nanoparticles B are produced by way of a method according to Kisner et al. (Kisner, A.; Lenk, S.; Mayer, D.; Mourzina, Y.; Offenhausser, A. J. Phys. Chem. C 2009, 113, 20143-20147). The second type of nanoparticles A are round homogeneous gold nanoparticles having an average diameter of 125 nm and a protective layer made of alkaline amine. The gold particles were purchased (http://www.nanopartz.com/ (part # E11-125).

A homogeneous mixture of these two different types of nanoparticles A and B is prepared. Toluene is the solvent used in this mixture. The percentage by weight of smaller nanoparticles B (10 nm) having the empirically determined melting point $S_{mB}$ of 280° C. in the mixture is 0.24%. The percentage by weight of larger nanoparticles A (125 nm) having the empirically determined melting point $S_{mA}$ of 350° C. in the mixture is 5.67%. The weight ratio between the two particle types A:B is approximately 23:1 wt/wt.

A drop having a volume of 1 microliter is applied to a glass substrate (microscope slide from ThermoScientific, dimensions: 76×26×1 (height) mm) using a lab pipette. The solvent is evaporated at room temperature within 5 minutes.

The glass substrate having the residue from the nanoparticle mixture dried thereon is heated on the heating plate at 300° C. for 5 minutes so as to cause the sintering of nanoparticles B, without melting particles A. Thereafter, the result is checked.

Figure 2:
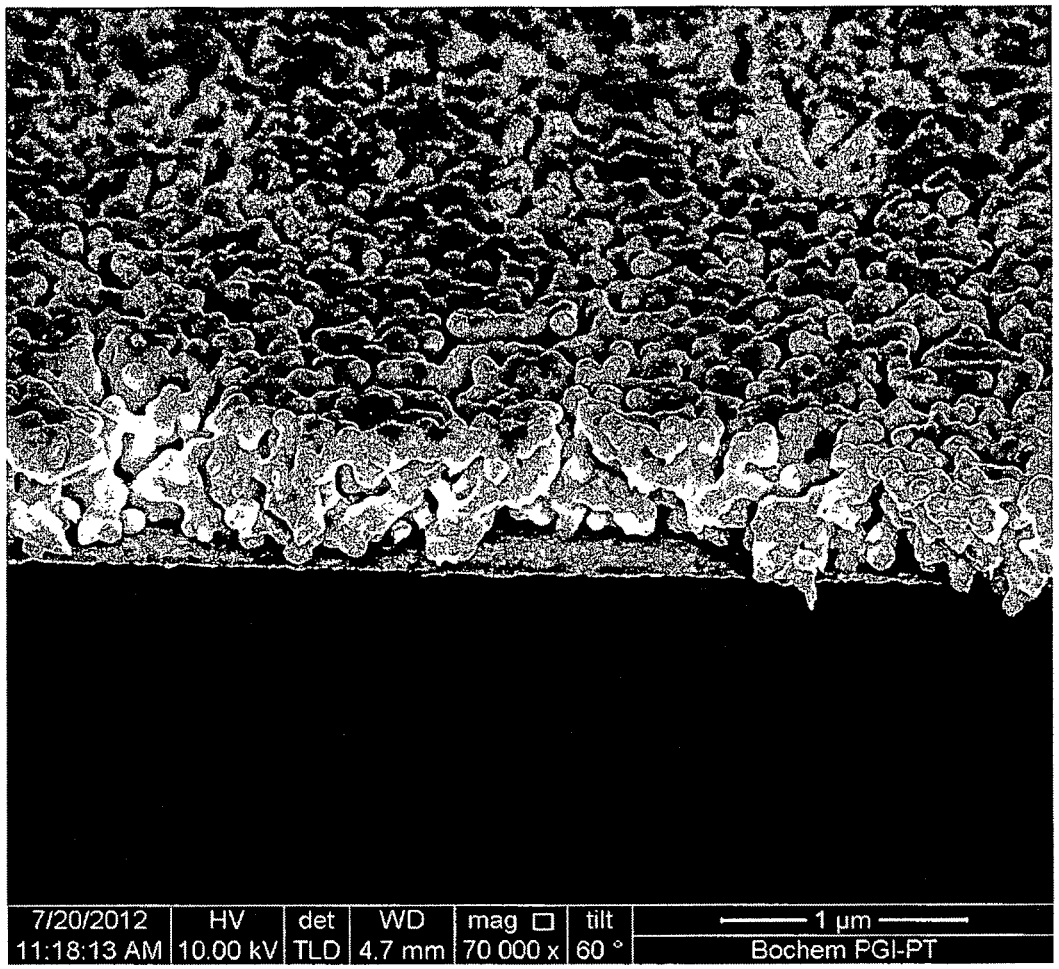
FIG. 2 shows scanning electron microscope images of a thin film made of gold particles having various sizes.

FIG. 2 shows a SEM image of the nanoporous layer. Evenly distributed lateral pores and vertical pores form a densely packed sponge-like structure. The pores extending to the substrate surface can be seen. Due to sintering, the residue changes to form a nanoporous layer having differing pore sizes in the range of 10 to 60 nm. The pore size is within the expected range. In the case of the densest ideal hexagonal sphere packing, interstice sizes of 28 nm and 52 nm (0.225*r for tetrahedral interstices and 0.4114*r for octahedral interstices) are anticipated. The particle size is used to accordingly adjust the size of the pores in the nanoporous layer in a defined manner.

The nanoporous layer produced according to the method of FIG. 1 is thereafter functionalized and, in a first alternative, used as an immunosensor. The produced nanoporous electrode is functionalized for this purpose by way of a thiol bond or by way of an amine bond or by physical methods, such as physisorption using specific antigens or antibodies. The functionalization can be carried out prior to sintering or after sintering in step d). In addition, electrical contact is made with the created electrode so as to allow electrical signals to be read out after an analyte has been bound to the functionalized layer. This is achieved by way of an ink jet printing method using conducting gold nanoparticles.

For the immunosensitive detection, a drop of blood or serum is applied to the electrode. The change in capacitance or resistance or impedance of the sensor is read out by way of electrochemical impedance spectroscopy and interpreted.

The nanoporous layer produced according to FIG. 1 is thereafter functionalized and, in a second alternative, used as an immunosensor against malaria, The produced nanoporous electrode is modified by further steps for this purpose.

The produced nanoporous layer is contacted with a conductor made of silver adhesive (Epo-Tek H20E-PFC) so as to generate an interface for electrical contact, Thereafter, the sensor is dried at 150° C. for 1 hour.

A glass ring (diameter 5 mm, height 1 mm) is glued to the nanoporous structure using polydimethylsiloxane (PDMS, Sylgard® 184) so as to form a reservoir. Thereafter, the sensor is dried at 150° C. for 1 hour.

Then, antigens against malaria, which is to say histidine rich protein 2 (HRP2), are immobilized on the nanoporous layer by physisorption. Specifically, 50 µl of a solution of HRP2 antigens (concentration=10 ng/µl) in a PBS buffer is applied to the nanoporous layer and incubated at 37° C. for 1 hour in the incubator at 100% humidity. Thereafter, the sensor is rinsed three times with deionized water so as to remove non-bound antigens.

Then, the unoccupied sites on the sensor are blocked with bovine serum albumin (BSA). Speciically, 50 µl of a 3% solution of BSA in PBS buffer is applied to the sensor and incubated at 37° C. for 1 hour in the incubator at 100% humidity. Thereafter, the sensor is rinsed again three times with deionized water so as to remove non-bound BSA. Then the sensor is dried.

In order to implement the measurement for the detection of malaria antibodies in the blood, an electric measuring amplifier (VSP-300 from BioLogic, PGSTAT from Autolab, CHI832B from CH Instruments) is required to carry out the impedance spectroscopy measurement. In addition, a reference electrode, such as Ag/AgCl, is needed to close the electric circuit.

A drop of blood, diluted or not, having a volume of 1 to 50 µl is applied to the sensor. Electrochemical impedance measurement by way of the closed circuit of modified nanoporous electrodes and Ag/AgCl reference electrodes is carried out, and more particularly in the frequency range of 100 Hz to 100 kHz. As a reference measurement, a drop of blood (1 to 50 µl) from the same patient is measured on a sensor that was produced in exactly the same manner, except for step 3, which is to say without specific HRP2 antigens against malaria.

The result of the reference sensor (without HRP2 antigens) is compared to the specifically modified sensor (with HRP2 antigens), and if a difference is found between the two, it is excluded that the test for HRP2 malaria antigens was positive. It is possible to implement microsensors against various antigens on one substrate.

Additional exemplary embodiments are described.

Exemplary embodiment using different nanoparticle sizes:

Two different types of nanoparticles are selected for the production of a nanoporous layer. One type of nanoparticle consists of round, homogeneous gold nanoparticles having an average diameter of 10 nm and a protective layer made of oleylamine, produced by the inventor by way of a method as described by Misner at al[1]. The second type of nanoparticle consists of round, homogeneous gold nanoparticles having an average diameter of either 40/60/80/100 or 125 nm and a protective layer made of alkaline amine, purchased from http://www.nanopartz.com/ (part # E11).

A mixture of these two types of nanoparticles is prepared. Toluene is the solvent used in this mixture. The percentage by weight of smaller nanoparticles (10 nm) having the empirically determined melting point $S_{m1}$ of 280° C. in the mixture is 0.24%. The percentage by weight of larger nanoparticles (40 to 125 nm) having the empirically determined melting point $S_{m2}$ of 320 to 350° C. in the mixture is 5.67%.

A drop having the volume of 1 microliter is applied to the glass substrate (microscope slide from ThermoScientific, dimensions: 76×26×1 (height) mm) using a lab pipette. The solvent is evaporated at room temperature within 5 minutes.

The glass substrate having the dried drop of the nanoparticle mixture is heated on the heating plate at 300° C. for 5 minutes so as to cause the sintering of nanoparticles.

The nanoporous layer formed is checked by way of scanning electron microscopy.

As a result of the sintering process, the dried drop changes into a nanoporous layer having different pore sizes in the range of 20 to 100 nm (average of approximately 50 nm, depending on the selected type of the second nanoparticle)

This nanoporous layer can moreover be used as an immunosensor, using electrochemical impedance spectroscopy as the read-out method.

Exemplary embodiment using different nanoparticle shapes:

Two different types of nanoparticles are selected for the production of a nanoporous layer. One type of nanoparticle consists of round, homogeneous gold nanoparticles having an average diameter of 10 nm and a protective layer made of oleylamine, produced by the inventor by way of a method as described by Misner et al[1]. The second type of nanoparticle consists of rod-shaped gold nanoparticles having an average diameter of either 25/40 or 50 nm and a length of 100/115/145/165/250±10 nm, and a protective layer made of alkaline amine (purchased from http://www.nanopartz.com/ (part #A12)).

A mixture of these two types of nanoparticles is prepared. Toluene is the solvent used in this mixture. The percentage by weight of round nanoparticles (10 nm) having the empirically determined melting point $S_{m1}$ of 280° C. in the mixture is 0.25%. The percentage by weight of rod-shaped nanoparticles (having a diameter of 25/40 or 50 nm and a length of 100/115/145/165/250±10 nm) having the empirically determined melting point $S_{m2}$ of 320 to 350° C. in the mixture is 6%.

A drop having the volume of 1 microliter is applied to the glass substrate (microscope slide from ThermoScientific, dimensions: 76×26×1 (height) mm) using a lab pipette. The solvent is evaporated at room temperature within 5 minutes.

The glass substrate having the dried drop of the nanoparticle mixture is heated on the heating plate at 300° C. for 5 minutes so as to cause the sintering of nanoparticles.

The formed nanoporous layer is checked by way of scanning electron microscopy.

As a result of the sintering process, the dried drop changes to form a nanoporous layer having different pore sizes in the range of 20 to 100 nm (average of approximately 50 nm, depending on the selected type of the second nanoparticle) In addition, by virtue of the shape thereof, the nanopores made of rod-shaped nanoparticles are anisotropic, which is to say the pores have a certain asymmetry.

Such an anisotropic nanoporous layer can be used in surface-enhanced Raman scattering (SERS), as is known from the literature, so as to generate plasmon resonances having certain spectral properties.

Additional steps for producing a functional immunological SERS sensor:

A glass ring (diameter 5 mm, height 1 mm) is glued to the nanoporous structure using polydimethylsiloxane (PDMS, Sylgard® 184) so as to form a reservoir. Thereafter, the sensor is dried at 150° C. for 1 hour.

Next, an optional step follows for immobilizing antigens against malaria. For this purpose, the histidine-rich protein 2 (HRP2), is immobilized on the nanoporous layer by physical adsorption. Specieially, 50 µl of a solution of HRP2 antigens (concentration=10 ng/µl) in a PBS (phosphate buffered saline) buffer is applied to the nanoporous layer and incubated at 37° C. for 1 hour (in the incubator at 100% humidity). Thereafter, the sensor is rinsed three times with deionized water so as to remove non-bound antigens. As an alternative, the cDNA fragments of the corresponding proteins (HRP2) can also be immobilized.

In the next step, the unoccupied sites on the sensor are blocked with bovine serum albumin (BSA). Specifically, 50 µl of a 3% solution of BSA in PBS buffer is applied to the sensor and incubated at 37° C. for 1 hour in the incubator at 100% humidity. Thereafter, the sensor is rinsed three times with deionized water so as to remove non-bound BSA. The sensor is subsequently dried and stored until it is used.

A SERS device (such as PSA from Real Time Analzyers, Inc.) is needed to implement the measurement for the detection of malaria antibodies/cDNA in the blood.

A drop of blood, diluted if necessary, having a volume of 1 to 50 µl is applied to the sensor. In the event that cDNA is immobilized instead of antibodies, the malaria parasites present in the blood must first be lysed. TritonX-100, for example, can be used for this step (5% of blood volume). The blood lysate is then applied to the sensor, the remaining steps being analogous to the procedure using immobilized antibodies.

After the incubation time of 15 minutes, the sensor is washed 3 times with PBS and 3 times with distilled water.

The sensor is excited with a SERS device-internal light source, and the SERS spectrum is recorded. As a reference measurement, a drop of blood (1 to 10 µl, including additional steps for the lysis in the case of cDNA detection) from the same patient is measured on a reference sensor. This reference sensor is produced analogously to the actual sensor, except that step 2 is omitted. This means that a sensor is formed without specific HRP2 antigens/cDNA against malaria The spectrum of the reference sensor (without HRP2 antigens/cDNA) is compared to the specifically modified sensor (with HRP2 antigens). Different responses of the two sensors indicate that the test for HRP2 malaria antigens was positive.

Additional steps for producing the functional chemical SERS sensor:

A glass ring (diameter 5 mm, height 1 mm) is glued to the nanoporous structure using polydimethylsiloxane (PDMS, Sylgard® 184) so as to form a reservoir, Thereafter, the sensor is dried at 150° C. for 1 hour.

1 to 50 µl of the solution containing the chemical substance to be tested (such as ethanol containing residues of toxic methanol) is applied to the chip.

The sensor is excited in a SERS device having an internal light source, and the SERS spectrum is recorded. A series of solutions having the same components (ethanol/methanol) and defined concentrations are applied to the chip and tested as reference measurements and for calibration purposes. The concentration of methanol in ethanol in the measured sample is determined based on the recorded SERS spectrum using the previously established calibration curve of the reference spectra.

As a result of the adaptation of the pore size and anisotropy of the conductive nanoporous layer, the properties of the surface plasmon resonance (SPR) change, and along with this, the optical properties of the nanoporous layer. This makes it possible to adapt the plasmon resonance frequency, and thus enables improved SERS signals from the detected molecules (antibodies/cDNA/chermical molecules).

(1) Kisner, A.; Lenk, S.; Mayer, D.; Mourzina, Y.; Offenhäusser, A, J. Phys. Chem. C 2009, 113, 20143-20147.

(2) Hsu, S. -W.; On, K.; Tao, A. R. J. Am. Chem. Soc. 2011, 133, 19072-19075.

Exemplary embodiment using different chemical composition for the nanoparticles:

Two different types of nanoparticles are selected for the production of a nanoporous layer. One type of nanoparticle consists of round, homogeneous conducting gold nanoparticles having an average diameter of 10 nm and a protective layer made of oleylamine, produced by the inventor by way of a method as described by Kisner at al[1]. The second type of nanoparticle consists of round, homogeneous semiconducting silicon nanoparticles having an average diameter of 30 nm, purchased from http://www.meliorum.com (product #09820).

A mixture of these two types of nanoparticles is prepared. Toluene is the solvent used in this mixture. The percentage by weight of round gold nanoparticles (10 nm) having the empirically determined melting point $S_{m1}$ of 280° C. in the mixture is 0.1%. The percentage by weight of round silicon nanoparticles (30 nm) having the melting point $S_{m2}$ of over 400° C. in the mixture is 10%.

A drop having the volume of 1 microliter is applied to the glass substrate (microscope slide from ThermoScientific, dimensions: 76×26×1 (height) mm) using a lab pipette. The solvent is evaporated at room temperature within 5 minutes.

The glass substrate having the dried drop of the nanoparticle mixture is heated on the heating plate at 300° C. for 5 minutes so as to cause the sintering of nanoparticles.

The formed nanoporous layer is checked by way of scanning electron microscopy.

As a result of the sintering process, the dried drop changes into a heterogeneous nanoporous layer having an average pore size of 10 nm. The semiconducting silicon nanoparticles are electrically connected by conductive sintered gold nanoparticles.

The composition of this nanoporous layer is a matrix made up of semiconducting silicon nanocrystals, which are electrically connected to each other by the gold nanoparticles. This layer can be used for applications in solar cells. With this method, it is possible to produce very thin printed layers of photosensitive elements having low sinter temperatures. The nano- allow light to pass to deeper silicon crystals, and thereby greater light absorption and accordingly higher efficiency for the solar cell.

Kisner, A.; Lank, S.; Mayer, D.; Mourzina, Y.; Offenhäusser, A. J. Phys. Chem. C 2009, 113, 20143-20147.

Exemplary embodiment using different chemical composition for the nanoparticles:

Two different types of nanoparticles are selected for the production of a nanoporous layer. One type of nanoparticle consists of round, homogeneous conducting gold nanoparticles having an average diameter of 5 nm and a protective layer made of citrate, purchased from http://www.nanopartz.com (product # A11C-5). The second type of nanoparticle consists of round, homogeneous conducting silver nanoparticles having an average diameter of 100 nm, purchased from http://www.sigmaaldrich.com (product # 730777).

A mixture of these two types of nanoparticles is prepared. Deionized water is the solvent used in this mixture. The percentage by weight of round gold nanoparticles (5 nm) having the melting point $S_{m1}$ of 180° C. in the mixture is 0.25%. The percentage by weight of round silver nanoparticles (100 nm) having the melting point $S_{m2}$ of 300° C. in the mixture is 5%.

A substrate comprising a soluble sacrificial layer is prepared. For example, a 4-inch glass substrate (borosilicate wafer, Collegewafers Inc.) is coated with a 10 nm chromium layer by way of a PVD (physical vapor deposition) method.

The prepared nanoparticle mixture is applied to the glass substrate coated with the chromium by way of spin coating. Approximately 10 ml of a nanoparticle solution is required for this, which can be spun on at a rotational speed of 3000 for 45 seconds. The solvent is evaporated at room temperature within 5 minutes.

The dried glass substrate coated with the nanoparticle mixture is heated on the heating plate at 230° C. for 5 minutes so as to sinter the nanoparticles.

The resulting nanoporous layer is checked by way of scanning electron microscopy. As a result of the sintering process, the dried drop changes to form a heterogeneous nanoporous layer having an average pore size of 10 nm. The conducting silver nanoparticles are electrically connected by conductive sintered gold nanoparticles.

The composition of this nanoporous layer is a matrix made up of conducting silver nanoparticles, which are electrically connected to each other by the gold nanoparticles. This layer can be used for applications in active nanoporous membranes.

The invention claimed is:

1. A method for producing a nanoporous layer on a substrate, comprising the following steps in order:
   a) selecting two types of particles, particles A and particles B, having different melting points;
   b) suspending both particles A and particles B in a solvent, thereby forming a suspension containing particles A and particles B;
   c) applying the suspension containing particles A and particles B to the substrate;
   d) melting, in a controlled manner, particles B having a lower melting point $S_{mB}$, without reaching a melting point $S_{mA}$ of particles A which is higher than $S_{mB}$, thereby forming a nanoporous layer on the substrate; and
   e) checking a surface of the nanoporous layer formed on the substrate.

2. The method according to claim 1, comprising selecting particles A and B such that difference in the melting points $S_{mA}$ and $S_{mB}$ is caused by a different chemical composition of particles A and B.

3. The method according to claim 1, comprising selecting particles A and B such that difference in the melting points $S_{mA}$ and $S_{mB}$ is caused by a different size of particles A and B.

4. The method according to claim 1, comprising selecting particles o A and B such that difference in the melting points $S_{mA}$ and $S_{mB}$ is caused by a different shape of particles A and B.

5. The method according to claim 1, wherein particles A and B are established at a weight ratio, with respect to each other, of A:B of 5:1 to 1000000:1 wt/wt.

6. The method according to claim 1, wherein particles A and B are selected such that the melting points $S_{mA}$ and $S_{mB}$ differ by at least 1 K.

7. The method according to claim 1, wherein steps a) to e) are carried out again after step e).

8. The method according to claim 1, wherein during or after production of the nanoporous layer, functionalization of the nanoporous layer is carried out using immunologically active antibodies or antigens.

9. The method according to claim 8, wherein the nanoporous layer after having been functionalized is contacted with a conductor, so as to conduct and detect electrical signals after immunologically active antigens or antibodies have bound to an analyte.

10. The method according to claim 1, wherein average diameters of particles A and B are each 1 nm to 10 μm.

11. The method according to claim 1, wherein particles A and B each comprise materials which conduct electricity.

12. The method according to claim 1, wherein particles A and B each comprise semiconductor materials.

13. The method according to claim 1, wherein particles A and B each comprise materials selected from the group consisting of gold, silver, platinum, aluminum oxide, silicon, copper, chromium, carbon, silver chloride, titanium, titanium oxide, iron oxide, magnesium oxide, zinc oxide, silicon oxide, silicon nitride and polyaniline.

* * * * *